(12) United States Patent
Sasaki

(10) Patent No.: US 10,070,781 B2
(45) Date of Patent: Sep. 11, 2018

(54) HAND-HELD CYCLODEVIATION MEASUREMENT DEVICE

(71) Applicant: TEIKYO UNIVERSITY, Tokyo (JP)

(72) Inventor: Kakeru Sasaki, Tokyo (JP)

(73) Assignee: TEIKYO UNIVERSITY, Tokyo (JP)

( * ) Notice: Subject to any disclaimer, the term of this patent is extended or adjusted under 35 U.S.C. 154(b) by 9 days.

(21) Appl. No.: 15/306,358

(22) PCT Filed: Apr. 24, 2015

(86) PCT No.: PCT/JP2015/062500
§ 371 (c)(1),
(2) Date: Feb. 7, 2017

(87) PCT Pub. No.: WO2015/163444
PCT Pub. Date: Oct. 29, 2015

(65) Prior Publication Data
US 2017/0196447 A1    Jul. 13, 2017

(30) Foreign Application Priority Data

Apr. 24, 2014   (JP) .................... 2014-090583
Sep. 11, 2014   (JP) .................... 2014-185222

(51) Int. Cl.
*A61B 3/08* (2006.01)
*A61B 3/00* (2006.01)

(52) U.S. Cl.
CPC .............. *A61B 3/08* (2013.01); *A61B 3/0075* (2013.01)

(58) Field of Classification Search
CPC .................. A61B 3/08; A61B 3/0075
(Continued)

(56) References Cited

U.S. PATENT DOCUMENTS

| 4,384,768 A | 5/1983 | Guzman |
| 4,838,676 A | 6/1989 | Buget et al. |
| 5,757,460 A | 5/1998 | Cockley |

FOREIGN PATENT DOCUMENTS

| CN | 1695547 | 11/2005 |
| GB | 2300487 | 6/1996 |

(Continued)

OTHER PUBLICATIONS

M. Ruttum, et al., Documenta Ophthalmologica, vol. 58, p. 131-139 (1984) Netherlands.
(Continued)

*Primary Examiner* — Jack Dinh
(74) *Attorney, Agent, or Firm* — Heslin Rothenberg Farley & Mesiti P.C.; Kristian E. Ziegler

(57) ABSTRACT

Provided is a cyclodeviation measurement device capable of performing quantitative measurement at low cost and capable of being used not only for diagnosis in an examination room and but also during a surgical operation in a surgical operating room, which has not been considered so far. In addition, provided is an improved device of the above device which can perform cyclodeviation measurement at a position other than the front by stabilizing vision fixation. The cyclodeviation measurement device includes a board, a pair of Maddox rods provided on the board so that at least one Maddox rod is rotatable, a manipulation means capable of freely rotating the rotatable Maddox rod, and an indication means indicating a rotation angle of the Maddox rod. The improved device includes a pair of a Maddox rod and a Bagolini striated lens instead of a pair of the Maddox rods.

4 Claims, 4 Drawing Sheets

(58) Field of Classification Search
USPC .......................................................... 351/201
See application file for complete search history.

(56) References Cited

FOREIGN PATENT DOCUMENTS

| | | |
|---|---|---|
| JP | 2001-346762 | 12/2001 |
| JP | 346762 | 12/2001 |
| JP | 2001346762 | 12/2001 |
| RU | 2089141 | 9/1997 |

OTHER PUBLICATIONS

International Search Report issued in PCT/JP2015/062500, dated Jul. 28, 2015.
VonNoorden et al., Binocular Vision and Ocular Motility: Theory and Management of Strabismus. Sixth Edition, Mosby Inc. 2002:194-198.
Olivier P. Von Noorden GK, Excyclotropia of the nonparetic eye in unilateral superior oblique muscle paralysis, American Journal of Ophthalmology, 1982, vol. 93, pp. 30-33.
Von Noorden G.K. Campos E.C., Binocular Vision and Ocular Motility Theory and Management of Strabismus. Sixth edition. Mosby Inc. 2002, pp. 194-198.
Oral workshop on Nov. 16, 2013 in Fukuoka, Japan; I. Reference(s): (i) Presentation slides used in the 54th Annual Meeting of the Japanese Orthoptic Congress, program No. II-1, on Nov. 16, 2013, and an English Abstract of the slides.

HAND-HELD CYCLODEVIATION MEASUREMENT DEVICE

TECHNICAL FIELD

The present invention relates to a hand-held cyclodeviation measurement device.

BACKGROUND

As methods for quantifying cyclodeviation in strabismus patient, Maddox double rod tests (Non-Patent Documents 1 and 2), major amblyoscopes (Non-Patent Document 2), new cyclo tests (Non-Patent Document 2), and the like are known.

The Maddox double rod test is performed by attaching two red and white Maddox rods to the trial frame and observing forward point light sources through the Maddox rods to perceive two linear light beams. By rotating one of the Maddox rods in the trial frame to measure a rotation angle until the two linear light beams become parallel to each other, so that the cyclodeviation can be quantitated. Although the methods are most widely used as quantitative methods because of low cost, since the scale of the trial frame is indicated in an increment of 5°, there is a problem in that detailed quantitation cannot be performed.

The major amblyoscope can perform detailed quantitation in an increment of 1°. However, it is assumed that the major amblyoscope is used in the installed state, and the device itself is extremely expensive.

The new cyclo test quantitates the cyclodeviation by observing a test chart printed with a half-moon figure arranged at a predetermined angle through red/green eyeglasses and allowing a patient to select the figure where the half-moon is viewed in parallel. There is a problem in that, in a case where horizontal strabismus or vertical strabismus is combined, it is difficult to perform the examination.

SUMMARY OF INVENTION

The inventor of the present invention has studied the improvement of a Maddox double rod test method for the purpose of developing a quantitative method of cyclodeviation capable of performing more quantitative measurement at low cost. The reason why the quantitatively of the Maddox double rod test is low is that the diameter of the Maddox rod is small and the scale of the trial frame is indicated in an increment of 5°. The inventors of the present invention have studied the enlargement of the Maddox rod, but as far as the inventors know, such approach has not been done so far. According to the inventor's estimation, the reason for this is that, in the trial frame in the related art, in order to perform an accurate measurement, the trial frame and the forehead surface of the subject need to be parallel to each other as much as possible, but since the temples and the nose pads are responsible for the function, there is a limitation in the upper limit of the Maddox rod.

In order to achieve a large Maddox rod, the inventor of the present invention has contrived a structure where a rectangular flat board that can be held by both hands is used instead of using an trial frame and the Maddox rod is interposed therebetween. It is difficult to keep the trial frame in the air while securing the parallel between the trial frame and the forehead surface of the subject in the trial frame in the state that the temples and the nose pads are removed. However, it is confirmed that this problem can be solved by using a flat board having a sufficient size and an appropriate weight. In addition, due to the adoption of the flat board, instead of the scale of the trial frame, the scale can be installed to a position sufficiently apart from the Maddox rod on the board, and thus, it is possible to further improve the quantitatively.

In this manner, the inventor of the present invention developed a cyclodeviation measurement device capable of performing more quantitative measurement while being inexpensive. However, at the beginning of the development, the inventor only assumed that the device is used for diagnosis in the examination room. However, since the device can perform the measurement without touching the patient, the inventor found that the cyclodeviation can be measured not only during the diagnosis in the examination room but also during the surgical operation in the surgical operating room. The advantage of the measurement of the cyclodeviation during the surgical operation is that, it is possible to check the correction effect of the surgical procedure, especially in a case where a plurality of surgical procedures are scheduled, it is possible to check the correction effect by the deviation amount every surgical procedure, and even in a case where the correction effect is insufficient, it is possible to perform extemporaneous responding such as changing or adding the surgical procedure while checking the residual strabismus angle. Therefore, the number of surgical operations can be minimized.

In addition, with respect to this point, it is considered that all various measurement methods known so far are inadequate for use in the surgical operating room, and the use during the surgical operation is not assumed.

For example, since a major amblyoscope is provided, it is originally impossible to bring the major amblyoscope into the surgical operating room, and since the major amblyoscope performs measurement in the sitting posture, the major amblyoscope cannot be used for the surgical operation performed in the supine position. Since the trial frame or the red/green eyeglasses need to be used in the Maddox double rod test or the new cyclo test, the surgical field becomes unclear, so that it is not considered that the Maddox double rod test or the new cyclo test is used during the surgical operation.

Therefore, an object of the present invention is to provide a cyclodeviation measurement device capable of perform quantitative measurement at low cost and capable of being used not only for diagnosis in an examination room but also during a surgical operation in a surgical operating room, which has not been considered so far. In addition, an object of the present invention is also to provide, as an improved device of the above-described cyclodeviation measurement device, the improved device capable of stabilizing vision fixation, so that cyclodeviation measurement can be performed in positions other than the front side (for example, in each of nine-directional eye positions).

According to the present invention, the above-described problems can be solved by the following configurations.

A cyclodeviation measurement device comprising a combination of any one of a Maddox rod and a Bagolini striated lens and a Maddox rod as a pair of combination lenses.

The cyclodeviation measurement device (hereinafter, referred to as an MM type cyclodeviation measurement device), including:

a board;

a pair of Maddox rods provided on the board so that at least one of the Maddox rods is rotatable;

a manipulation means capable of freely rotating the rotatable Maddox rod; and an indication means indicating a rotation angle of the Maddox rod.

The cyclodeviation measurement device, wherein one of the Maddox rods is interchangeable with the Bagolini striated lens.

The cyclodeviation measurement device (hereinafter, referred to as an MB type cyclodeviation measurement device), including:
    a pair of a Maddox rod and a Bagolini striated lens,
    a lens holding means capable of holding the Maddox rod and the Bagolini striated lens so that the Maddox rod is rotatable;
    a manipulation means capable of freely rotating the Maddox rod; and
    an indication means indicating a rotation angle of the Maddox rod.

The cyclodeviation measurement device, wherein the Bagolini striated lens is interchangeable with the Maddox rod.

A cyclodeviation measurement device according to the present invention (including an MM type and an MB type if not particularly excluded) is inexpensive and can perform quantitative measurement.

A cyclodeviation measurement device according to the present invention can be used not only in a diagnosis in an examination room but also in a surgical operating room. Since the cyclodeviation measurement device can be used to check the correction effect of a surgical procedure during the surgical operation, the number of surgical operations can be minimized. In a well-known cyclodeviation measurement method of the related art, there is no measurement method which can be used in a surgical operating room. The cyclodeviation measurement device according to the present invention is an extremely innovative measurement device capable of being used during the surgical operation which has not been considered in the method of the related art which has been used only in diagnosis so far.

In addition, an MB type cyclodeviation measurement device according to the present invention can perform the cyclodeviation measurement in positions other than the front side by stabilizing vision fixation, for example, in each of nine-directional eye positions.

BRIEF DESCRIPTION OF THE DRAWINGS

FIG. 7a is a view in a case where there is no cyclodeviation, and FIG. 7b is a view in a case where there is cyclodeviation. In any one of FIGS. 7a and 7b, the upper side is a linear light beam originated from a Bagolini striated lens, and the lower side is a linear light beam originated from a Maddox rod.

DETAILED DESCRIPTION

Hereinafter, with respect to cyclodeviation measurement devices according to the present invention, an MM type device will be described, and after that, an MB type device will be described.

Figure 1:
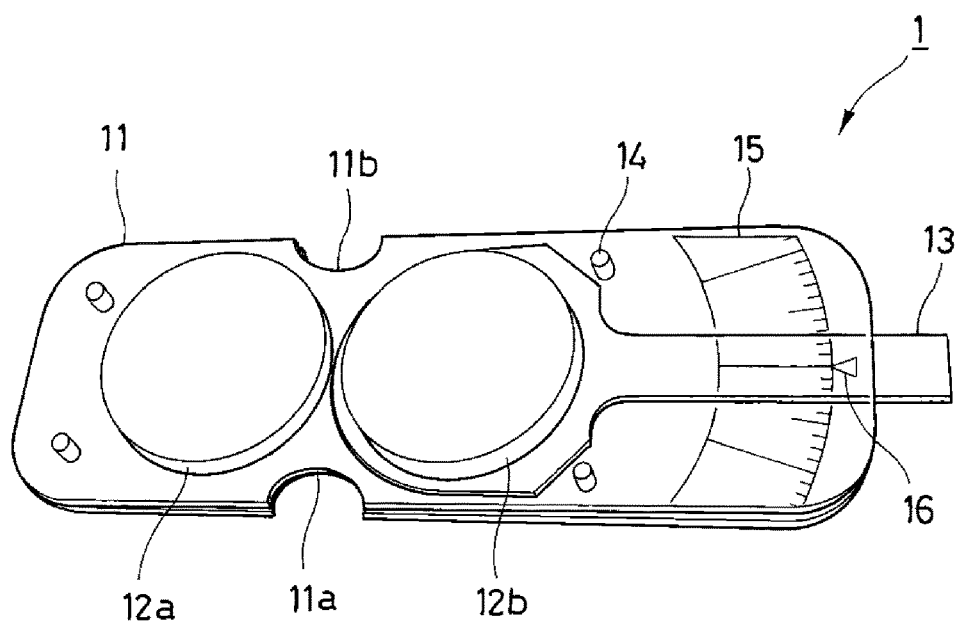
FIG. 1 is a perspective diagram schematically illustrating an embodiment of an MM type cyclodeviation measurement device according to the present invention.
Figure 2:
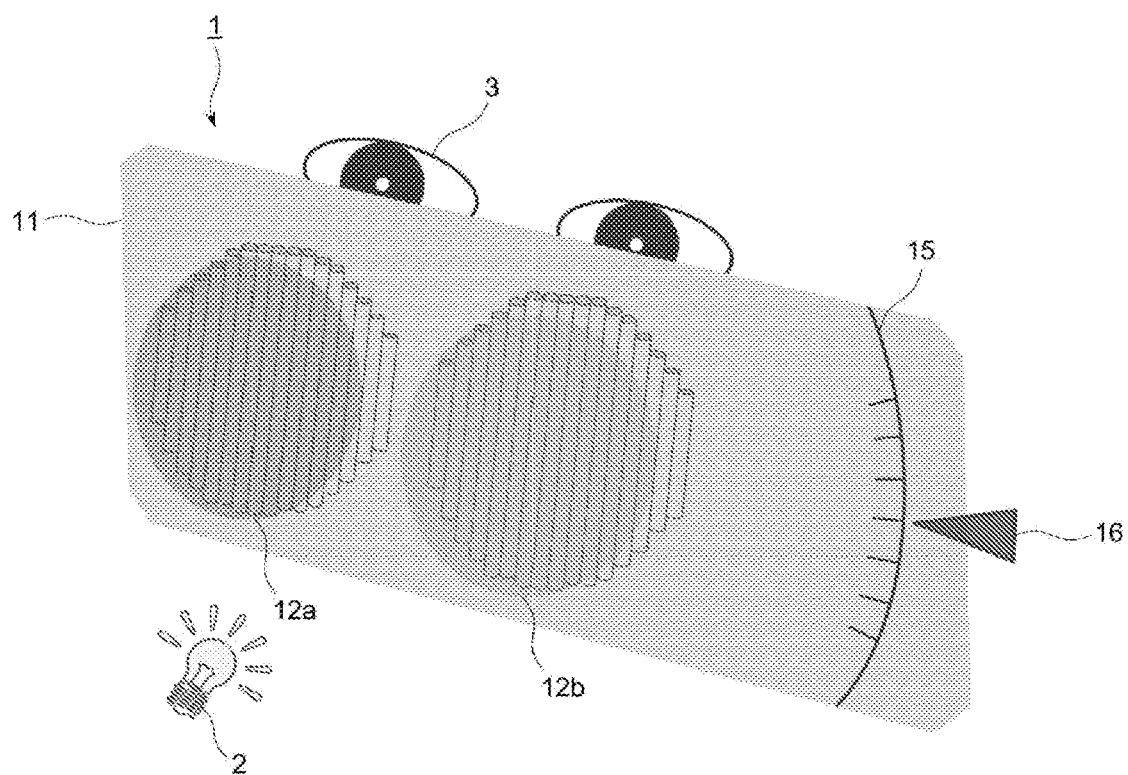
FIG. 2 is an explanatory diagram schematically illustrating a method of using the device illustrated in FIG. 1.

FIG. 1 is a perspective diagram schematically illustrating an embodiment of an MM type cyclodeviation measurement device according to the present invention, and FIG. 2 is an explanatory diagram schematically illustrating a method of using the device illustrated in FIG. 1.

In a cyclodeviation measurement device 1 illustrated in FIGS. 1 and 2, a pair of Maddox rods 12a and 12b are installed to be interposed between two transparent flat boards 11, and one Maddox rod 12a is fixed to the board 11. On the other hand, the other Maddox rod 12b is attached to the board 11 so that the Maddox rod is freely rotatable by manipulating the manipulation knob 13 connected thereto. The two flat boards 11 are integrated by metal pins 14. The manipulation knob 13 may be integrated with the scale 15 installed on the boards 11 to function as an indication means indicating a rotation angle of the Maddox rod 12b. A triangular indication mark 16 installed on the manipulation knob 13 indicates a specific position of the scale 15, so that the rotation angle can be read. Different color filters (for example, a red filter for the fixed Maddox rod 12a and a green filter for the rotatable Maddox rod 12b) integrated with the respective Maddox rods are inserted between the Maddox rods 12a and 12b and the board 11. As desired, a level (not shown) may be provided.

Figure 3A:
FIG. 3 is an explanatory diagram illustrating a view of a light source target when the MM type cyclodeviation measurement device according to the present invention is mounted, a is a view in a case where there is no cyclodeviation, and b is a view in a case where there is cyclodeviation.
Figure 3B:
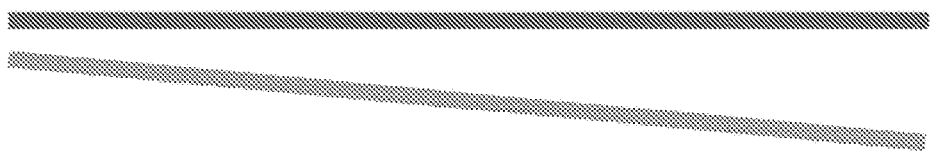

The Maddox rods 12a and 12b illustrated in FIGS. 1 and 2 (in FIG. 2, the manipulation knob 13 and the like are omitted) have a structure obtained by aligning a plurality of cylindrical lenses in parallel without gap and cutting in a circular shape. The cyclodeviation measurement device 1 is arranged between the point light source 2 and the two eyes 3 of the subject, and the linear light beam perpendicular to the longitudinal direction of the Maddox rods is perceived by observing the point light source 2 through the Maddox rod group. For example, one eye (non-paralytic eye in the case of paralytic strabismus) of the subject is defined as a fixed eye. If the point light source 2 is observed in the state that the Maddox rod 12a in the red filter side is maintained in front of the eye of the subject so that the Maddox rod is located in front of the fixed eye and the rotation angle of the Maddox rods 12a and 12b is adjusted so that the longitudinal directions of the Maddox rods are perpendicular, with respect to a subject having no cyclodeviation, as illustrated FIG. 3a, two linear light beams (for example, the upper red beam and the lower green beam) are observed to be horizontal or parallel. In addition, with respect to a subject having no vertical strabismus, since two linear light beams overlap with each other, in general, a prism lens (for example, a Fresnel membrane prism having about 10 PD) attached to one Maddox rod (for example, the Maddox rod in the non-fixed eye side) may be used so that the vertical deviation becomes clear. In a case where the two linear light beams are not parallel to each other (FIG. 3b), the angle at the time when the two linear light beams are parallel to each other by rotating the Maddox rod 12b in the non-fixed eye side is quantitated as cyclodeviation. In FIG. 1, the scale indicated in an increment of 1° indicates the angle of rotation.

As the Maddox rods used in the cyclodeviation measurement device according to the present invention, besides Maddox rods having a shape of an assembly of cylindrical lenses (having a circular cross-section) illustrated in FIG. 2, well-known Maddox rods in the related art may be used, and for example, a Maddox rod having a shape (namely, one surface has a waves-shaped plane) of an assembly of semi-circular cylindrical lenses (having a semi-circular cross-section) may be exemplified.

As shapes of the Maddox rods, with respect to the Maddox rod which is arranged to be rotatable, besides a circular shape illustrated in FIGS. 1 and 2, any rotatable shape may not particularly be limited, and for example, a polygonal shape approximate to a circle may be exemplified. With respect to the Maddox rod which is not required to be rotatable but arranged to be fixed, besides a circular shape, various shapes such as an elliptical shape or a polygonal shape may be exemplified.

Any filters having different colors which are inserted between the Maddox rods and the board may be used.

With respect to a pair of the Maddox rods used in the cyclodeviation measurement device according to the present invention, at least one Maddox rod is configured to be rotatable. Namely, as illustrated in FIGS. 1 and 2, one Maddox rod may be configured to be fixed, and the remaining Maddox rod may be configured to be rotatable. Alternatively, both Maddox rods may be configured to be rotatable.

The cyclodeviation measurement device according to the present invention is generally used so that the fixed Maddox rod is located in front of the fixed eye of the subject. However, as illustrated in FIGS. 1 and 2, even in a case where one Maddox rod is configured to be fixed and the remaining Maddox rod is configured to be rotatable, although any one of right and left eyes is a fixed eye, the cyclodeviation measurement can be performed.

In a case where both Maddox rods are configured to be rotatable, only one Maddox rod is rotated, and the angle may be quantitated as the cyclodeviation. Alternatively, both Maddox rods are rotated, and the relative angle may be quantitated as the cyclodeviation.

With respect to the Maddox rods used in the cyclodeviation measurement device according to the present invention, in a case where the shape is circular, since it is preferable that the centers of the Maddox rods are located at the centers of the pupils, the diameter of the Maddox rod is generally in a range of 4 cm to 8 cm, preferably in a range of 5.5 cm to 7 cm, more preferably, in a range of 6 cm to 6.5 cm. This is because the average distance between the centers of the pupils of a human is about 62 mm. In addition, in a case where the diameter is smaller than 4 cm, the quantitatively may be deteriorated. In a case where the diameter is larger than 8 cm, since the measurement is performed in a periphery greatly deviated from the center of each Maddox rod, the quantitatively may be deteriorated.

The arrangement interval between the two Maddox rods also depends on the diameter of the Maddox rod. In general, the arrangement interval is in a range of 0 cm (namely, in contact with each other) to 3 cm, preferably in a range of 0 cm to 2 cm. For example, in a case where the diameter of the Maddox rod is equal to or larger than 6 cm, it is preferable that the two Maddox rods are in contact with each other.

As the manipulation means capable of freely rotating the Maddox rod and the indication means indicating the rotation angle of the Maddox rod, which can be used the cyclodeviation measurement device according to the present invention, any manipulation means which can freely rotate the rotatable Maddox rod according to intention of a manipulator (for example, a person carrying out the measurement or a subject) and any indication means which can indicate the rotation angle are not particularly limited.

Figure 4:
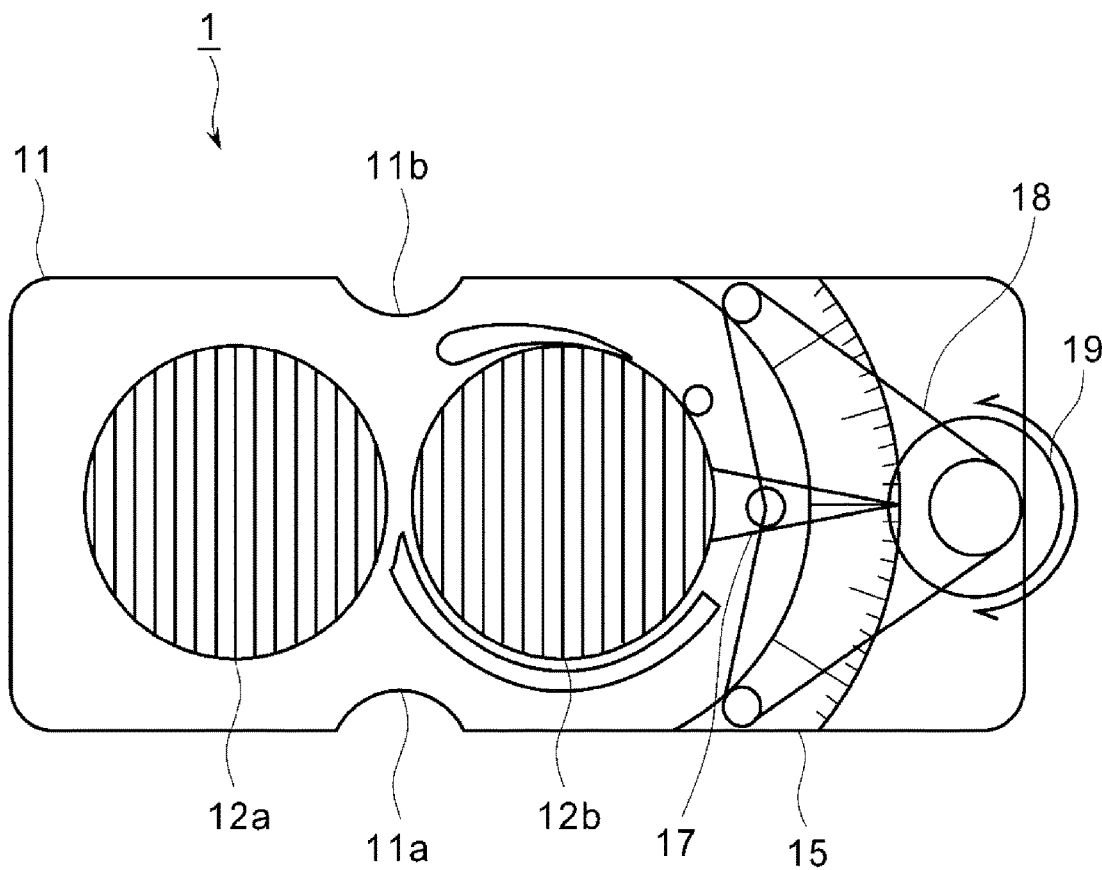
FIG. 4 is a plan diagram schematically illustrating another embodiment of the MM type cyclodeviation measurement device according to the present invention.

Another embodiment of the MM type cyclodeviation measurement device according to the present invention is illustrated in FIG. 4.

In the embodiment illustrated in FIG. 4, a pair of Maddox rods 12a and 12b are also interposed between two transparent flat boards 11. One Maddox rod 12a is fixed to the board 11, and the other Maddox rod 12b is attached to the board 11 so that the Maddox rod is rotatable. The board 11 is provided with a scale 15, and the Maddox rod 12b is attached with an indication member 17. The indication member 17 is attached with a wire 18 (or a string or the like), and by rotating a rotation dial 19 attached to the board 11, the Maddox rod 12b and the indication member 17 can be allowed to be rotated.

As the manipulation means and the indication means, for example, besides a combination of a manipulation knob, a manipulation stick, a manipulation bar, or the like connected to the Maddox rod and a scale provided to the board illustrated in FIGS. 1 and 2 or a combination of a rotation dial, an indication member, and a wire illustrated in FIG. 4, for example, a digital indicator, a speaker, a printer, or the like may be exemplified. The indication means is not necessarily provided to the board. For example, an indication means connected to the board in a wired manner or an indication means connected to the board in a wireless manner may constitute the cyclodeviation measurement device according to the present invention (or the cyclodeviation measurement system according to the present invention).

In addition, as the manipulation means capable of freely rotating the Maddox rod, for example, a manipulation means rotating the Maddox rod according to a rotation angle input from an input means provided to the board or an input means connected to the board in a wired or wireless manner may be exemplified. In this case, the input means also may serve as an indication means, or an independent indication means may be provided.

With respect to the board used in the cyclodeviation measurement device according to the present invention, as long as a pair of Maddox rods can be arranged and the cyclodeviation measurement can be performed, a shape, a size, and a material thereof are not particularly limited.

As the shape of the board, a shape which is easy to hold in the air with both hands and can be easily set to be parallel to the forehead of the subject is preferred. For example, a substantially polygonal shape including a substantially tetragonal shape such as a substantially rectangular shape or a substantially square shape, a substantially elliptical shape, a substantially circular shape, and the like may be exemplified. In a portion (preferably, one portion or two portions) of the outer periphery of the board, notches 11a and 11b for avoiding interference with the nose may be provided at positions which are likely to be in contact with the nose.

The size of the board may be mainly determined according to the size of the Maddox rod. For example, in a case where the board has a rectangular shape, the length of the long side is in a range of 10 cm to 30 cm, and the length of the short side is in a range of 5 cm to 15 cm. In addition, in a case where the board has a flat shape, the thickness thereof is, for example, in a range of 1 mm to 3 cm. In addition, the board may have a film shape.

With respect to the material of the board, as long as the desired effect of the device according to the present invention is achieved, the material is not particularly limited. For example, plastic, reinforced glass, paper, metal, fabric, rubber, wood, or the like may be exemplified. In terms of visibility of the Maddox rods or the indication means, a transparent material is preferably used, and in addition, in terms of use during the surgical operation, a sterilizable material is preferably used. As the materials, for example, transparent plastic, reinforced glass, or the like may be exemplified.

As described above, the MM type cyclodeviation measurement device according to the present invention is described. Subsequently, as an improved device, an MB type cyclodeviation measurement device according to the present invention will be described.

In the MB type cyclodeviation measurement device according to the present invention, a pair of the Maddox rods in the MM type cyclodeviation measurement device according to the present invention are replaced with a pair of a Maddox rod and a Bagolini striated lens. Except for the replacement, the above description on the MM type cyclodeviation measurement device according to the present invention can be applied to the MB type cyclodeviation measurement device according to the present invention as it is within the technical common sense of the ordinarily skilled in the related art.

Figure 5:
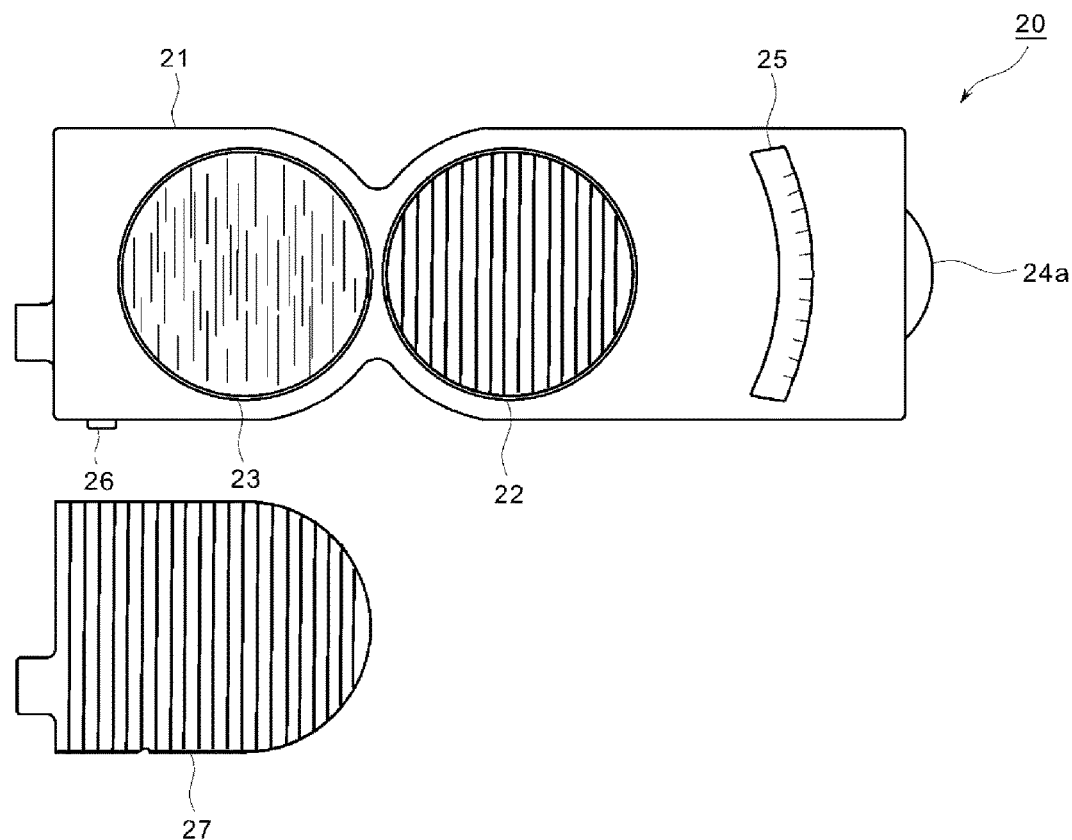
FIG. 5 is a perspective diagram schematically illustrating an embodiment of an MB type cyclodeviation measurement device according to the present invention, together with a Maddox rod which is interchangeable with a Bagolini striated lens.
Figure 6:
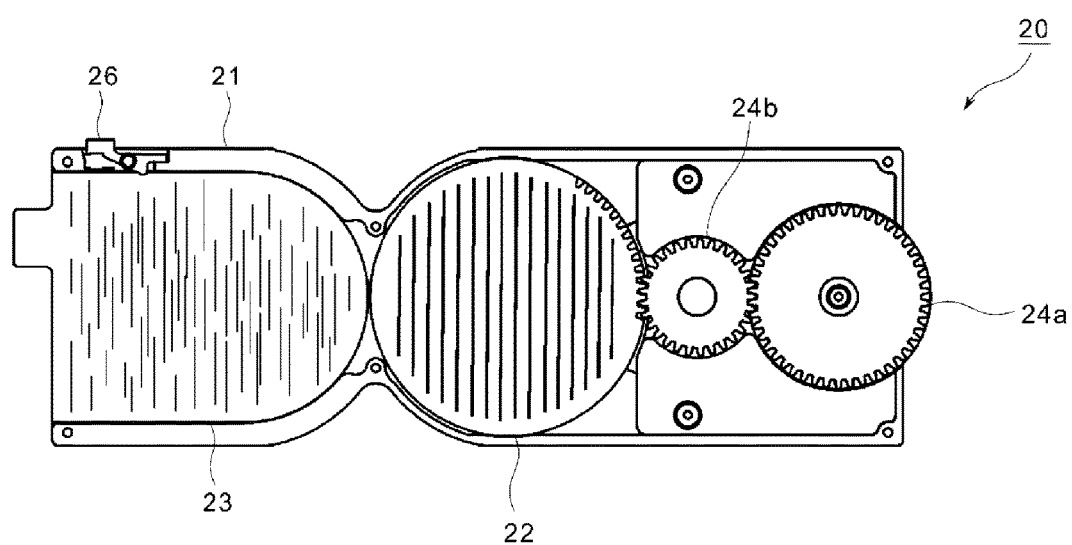
FIG. 6 is a perspective diagram schematically illustrating an internal structure of the device illustrated in FIG. 5.

FIG. 5 is a perspective diagram schematically illustrating an embodiment of the MB type cyclodeviation measurement device according to the present invention together with an Maddox rod which is interchangeable with a Bagolini striated lens. FIG. 6 is a perspective diagram schematically illustrating an internal structure of the device illustrated in FIG. 5.

In the cyclodeviation measurement device 20 illustrated in FIGS. 5 and 6, a pair of a Maddox rod 22 and a Bagolini striated lens 23 are installed to be interposed between two flat boards 21 where a pair of circular windows are provided at positions corresponding to two eyes. In the device illustrated in FIGS. 5 and 6, since the board 21 is colored (for example, black), the circular windows are provided. However, in a case where the board is transparent, the circular windows may not be provided.

The Maddox rod 22 is attached to the board 21 so that the Maddox rod can be freely rotated through rotating gears 24b by manipulating a rotation dial 24a. The rotation angle of the Maddox rod 22 can be read from an indication member (not shown) connected to the Maddox rod 22 which indicates a specific position of a scale 25 on the board. The Bagolini striated lens 23 is not rotated with respect to the board 21, and by manipulating a stopper 26, the Bagolini striated lens can be detached from the board 21. Instead of the detached Bagolini striated lens 23, a separately prepared Maddox rod 27 is mounted, so that the cyclodeviation measurement device can be used as the MM type cyclodeviation measurement device. A filter (for example, a green filter) integrated with the Maddox rod is inserted between the Maddox rod 22 and the board 21. In the device illustrated in FIGS. 5 and 6, a color filter is used. Alternatively, the board or the Maddox rod may be directly colored. As desired, a level (not shown) may be provided.

Figure 7A:
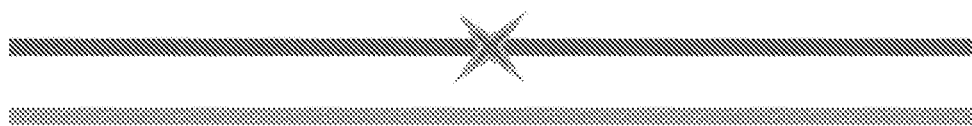
FIGS. 7a and 7b are explanatory diagrams illustrating views of a light source target when the MB type cyclodeviation measurement device according to the present invention is mounted, where
Figure 7B:
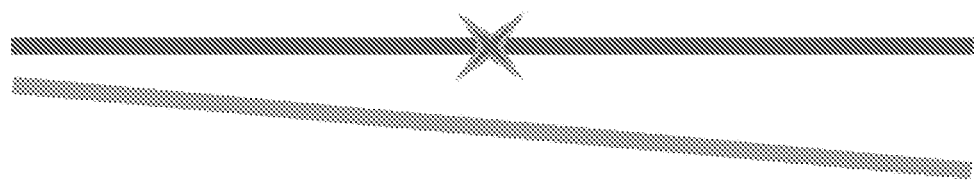

The Bagolini striated lens 23 is a lens used for Bagolini striated lens examination of diagnosing abnormalities in the retina and is a lens with linear scratches on a colorless transparent or colored transparent glass. By observing the point light source located at the front through the Bagolini striated lens (for example, red) arranged so that the scratch direction is vertical, one linear light beam perpendicular to the longitudinal direction of the scratch (namely, one horizontal linear light beam) is perceived. In the Maddox rod, the linear light beam having a constant width which is perpendicular to the longitudinal direction of the Maddox rod is perceived (refer to FIG. 3). In the Bagolini striated lens, the linear light beam which is grown in two directions from the point light source (luminescent spot) as a center as illustrated in the upper portion of FIG. 7a or the upper portion of FIG. 7b is perceived. Therefore, the above-described luminescent spot can be used as a target of stabilizing the vision fixation. The cyclodeviation measurement device 20 is arranged between the point light source and the two eyes of the subject and is held in front of the eyes of the subject so that the Bagolini striated lens 23 is located at the eye defined as a fixed eye. If the point light source 2 is observed in the state that the rotation angle of the Maddox rod 22 (for example, green) is adjusted so that the longitudinal direction of the Maddox rod is vertical, in the case of the subject having no cyclodeviation, as illustrated in FIG. 7a, the two linear light beams (for example, a red light beam (the upper beam) originated from the Bagolini striated lens and a green light beam (the lower beam) originated from the Maddox rod) are observed to be horizontal or parallel. In a case where the two linear light beams are not parallel to each other (FIG. 7b), by rotating the Maddox rod 22 in the non-fixed eye side, the angle at the time when the two linear light beams become parallel to each other is quantitated as the cyclodeviation.

In the MB type cyclodeviation measurement device, in a case where the point light source is arranged at the front, the linear light beam originated from the Bagolini striated lens horizontally passes through the center of the field of view, and the luminescent spot occurs in the vicinity of the center of the field of view. On the other hand, in a case where the point light source is arranged to be deviated from the front, for example, in a case where the point light source is arranged in the upper portion at the front, the linear light beam originated from the Bagolini striated lens horizontally passes through the upper portion of the field of view, and the luminescent spot occurs in the vicinity of the center of the field of view. In addition, in a case where the point light source is arranged to be deviated in the rightward direction at the front (as viewed from the subject), the linear light beam originated from the Bagolini striated lens horizontally passes through the center of the field of view, and the luminescent spot occurs at the position deviated in the rightward direction in the field of view. Therefore, in the MB type cyclodeviation measurement device, the position of the linear light beam originated from the Bagolini striated lens can be changed by adjusting the position of the point light source. Accordingly, if the linear light beam (particularly, the luminescent spot) is used as a target, it is possible to stabilize the vision fixation in an arbitrary direction. This denotes that the cyclodeviation measurement in arbitrary directions can be individually performed. For example, with respect to each of the nine-directional eye positions, the cyclodeviation measurement can be performed.

With respect to shapes and sizes of the Bagolini striated lens and the Maddox rod used in the cyclodeviation measurement device according to the present invention, the above description on the Maddox rod in the MM type cyclodeviation measurement device can be applied as it is.

The Bagolini striated lens used in the cyclodeviation measurement device according to the present invention may be configured to be rotatable or may be configured to be fixed so as not to be rotated. In terms of the stabilization of vision fixation, in general, the Bagolini striated lens is configured to be fixed so as not to be rotated.

With respect to the manipulation means and the indication means which may be used in the MB type cyclodeviation measurement device, the above description on the manipulation means and the indication means in the MM type cyclodeviation measurement device can be applied as it is.

In the MB type cyclodeviation measurement device, as the lens holding means holding the Maddox rod and the Bagolini striated lens, the board used in the MM type cyclodeviation measurement device may be used, or a lens holding means other than the board may be used.

In the case of using the board used in the MM type cyclodeviation measurement device, the above description on the board in the MM type cyclodeviation measurement device can be applied as it is.

As the lens holding means other than the board, for example, an trial frame may be exemplified.

EXAMPLES

Hereinafter, the present invention will be described in detail with reference to examples, but the examples do not limit the scope of the present invention.

Example 1: Evaluation of MM Type Cyclodeviation Measurement Device According to Present Invention in Diagnosis In this Example and the following Example 2, the MM type cyclodeviation measurement device illustrated in FIG. 1 was used as the device according to the present invention. The board is made of a transparent acrylic plate of 26 cm×10 cm×1 cm. The diameter of the Maddox rod obtained by arranging transparent acrylic rods having a diameter of 2 mm without gap is 7 cm.

In this example, in order to evaluate the quantitatively of the MM type cyclodeviation measurement device according to the present invention, the cyclodeviation measurement was performed on a normal person group of 20 subjects who were observed to have no ophthalmologic disease other than refractory abnormality (6 men and 14 women; 22 to 30 years old, and average age of 23.3 years) as a normal control group and a patient group of 20 subjects who were recognized to have cyclotropia (12 men and 8 women; 8 to 79 years old, and average age of 54.8 years). The patient group is a group of patients having a cyclodeviation of 2° or more at the primary eye position detected in the major amblyoscope examination. The details of the strabismus are that 16 subjects have monocular superior oblique palsy, 3 subjects have bilateral superior oblique palsy, and one subject has monocular superior rectus muscle palsy.

As the evaluation procedure, a self-conscious strabismus angle examination (one time per patient) at the primary eye position by the major amblyoscope and a cyclodeviation measurement (one time per patient) in the sitting posture and the supine position by the device according to the present invention were performed, and comparison of the values of cyclodeviation was performed. At this time, with respect to the device according to the present invention, the time required for the examination every patient was measured. As a target of the major amblyoscope, a cross-shaped figure for the cyclodeviation measurement was used.

For the statistical analysis, one-way analysis of variance was used. The result for the normal person group is listed in Table 1, and the result for the cyclotropia patient group is listed in Table 2.

TABLE 1

| No. | Age | Sex | Major amblyoscope | Present invention (sitting) | Present invention (supine) |
| --- | --- | --- | --- | --- | --- |
| 1 | 22 | F | Ex 1° | 0° | 0° |
| 2 | 22 | M | 0° | 0° | 0° |
| 3 | 28 | F | 0° | 0° | 0° |
| 4 | 29 | M | 0° | 0° | 0° |
| 5 | 21 | F | 0° | 0° | 0° |
| 6 | 24 | M | 0° | 0° | 0° |
| 7 | 21 | F | 0° | 0° | 0° |
| 8 | 30 | F | 0° | 0° | 0° |
| 9 | 22 | F | Ex 1° | Ex 1° | Ex 1° |
| 10 | 22 | M | 0° | 0° | 0° |
| 11 | 22 | F | 0° | 0° | 0° |
| 12 | 22 | F | 0° | 0° | 0° |
| 13 | 21 | F | 0° | 0° | 0° |
| 14 | 22 | F | 0° | 0° | 0° |
| 15 | 25 | F | 0° | 0° | 0° |
| 16 | 23 | M | 0° | 0° | 0° |
| 17 | 22 | F | 0° | 0° | 0° |
| 18 | 22 | F | 0° | 0° | 0° |
| 19 | 21 | M | 0° | 0° | 0° |
| 20 | 22 | F | 0° | 0° | 0° |

TABLE 2

| No. | Age | Sex | Diagnosis | Major amblyoscope | Present invention (sitting) | Present invention (supine) |
| --- | --- | --- | --- | --- | --- | --- |
| 1 | 59 | F | Left) SOP | Ex 3° | Ex 3° | Ex 3° |
| 2 | 75 | M | Bilateral) SOP | Ex 18° | Ex 19° | Ex 20° |
| 3 | 40 | M | Bilateral) SOP | Ex 13° | Ex 13° | Ex 14° |
| 4 | 66 | M | Right) SOP | Ex 5° | Ex 5° | Ex 5° |
| 5 | 39 | F | Right) SOP | Ex 8° | Ex 7° | Ex 7° |
| 6 | 32 | F | Right) SOP | Ex 2° | Ex 3° | Ex 3° |
| 7 | 40 | M | Bilateral) SOP | Ex 10° | Ex 10° | Ex 12° |
| 8 | 58 | M | Right) SOP | Ex 10° | Ex 11° | Ex 10° |
| 9 | 66 | M | Right) SOP | Ex 3° | Ex 3° | Ex 2° |
| 10 | 58 | M | Right) SOP | Ex 6° | Ex 5° | Ex 5° |
| 11 | 65 | F | Right) SOP | Ex 7° | Ex 7° | Ex 5° |
| 12 | 70 | M | Right) SOP | Ex 5° | Ex 4° | Ex 5° |
| 13 | 48 | M | Left) SOP | Ex 7° | Ex 8° | Ex 8° |
| 14 | 58 | F | Left) SOP | Ex 12° | Ex 13° | Ex 13° |
| 15 | 8 | F | Left) SOP | Ex 3° | Ex 3° | Ex 5° |
| 16 | 31 | F | Right) SRMP | Ex 16° | Ex 15° | Ex 14° |
| 17 | 67 | M | Left) SOP | Ex 11° | Ex 12° | Ex 13° |
| 18 | 65 | F | Left) SOP | Ex 3° | Ex 3° | Ex 3° |
| 19 | 79 | M | Right) SOP | Ex 4° | Ex 4° | Ex 5° |
| 20 | 71 | M | Left) SOP | Ex 12° | Ex 13° | Ex 14° |

SOP: Superior oblique palsy
SRMP: Superior rectus muscle palsy

As the result (average value±standard deviation) of the examination for the normal person group of 20 subjects listed in Table 1, the value by the major amblyoscope was Ex0.1°±0.3°, the value by the device according to the present invention at the sitting posture was Ex0.1°±0.2°, and the value by the device according to the present invention at the supine position posture was Ex0.1°±0.2°. As the result for the cyclotropia patient group of 20 subjects listed in Table 2, the value by the major amblyoscope was Ex7.9°±4.6°, the value by the device according to the present invention at the sitting posture was Ex8.1°±4.8°, and the value by the device according to the present invention at the supine position posture was Ex8.3°±4.9°. With respect to the entire normal person group (p=0.38) and the cyclotropia patient group (p=0.27), there was recognized no meaningful difference between the examinations.

Among the well-known measurement methods in the related art, the measurement methods by the major amblyoscope are superior in that detailed quantitation can be performed in an increment of 1°, the degree of binocular separation is strong, and the cyclodeviation for the latent portion can also be measured. However, it is considered that the device according to the present invention can also detect the amount of cyclodeviation including the latent portion because the state of binocular separation is strong. The validity was confirmed from the fact that the quantitatively is as high as that of the major amblyoscope. In addition, in the device according to the present invention, it was confirmed that there is no difference in the measurement value between the sitting posture (at a general diagnosis period) and the supine position posture (during the surgical operation) and the measurement can be performed at any posture.

With respect to the time required for the measurement by the device according to the present invention, in the first examination, the time was average 54.53 seconds including the time for describing the examination, and in the second examination and the following examinations where the patient had already understood the examination method, the time was average 26.33 seconds.

In the case of performing the examination during the surgical operation, short examination time is essential. In the examination by the device according to the present invention, if the patient is allowed to understand the examination method through the explanation in advance, the measurement can be completed almost in less than 30 seconds, so that quantitation can be performed very fast.

Example 2: Use of MM Type Cyclodeviation Measurement Device According to Present Invention During Strabismus Surgical Operation In this example, with respect to a female patient (75 years old at the time of the second surgical operation) whom two times of the strabismus surgical operation are performed on, the examination therebetween and the result of the surgical operations are illustrated. The first surgical operation is performed without using the device according to the present invention, and the second surgical operation is performed by using the device according to the present invention.

First Surgical Operation

As doctor's note at the first visit, the visual acuities of the right and left eyes were (1.2×+1.50 D cyl+1.50 D15°) and (1.2×+1.50 D cyl+0.50 D165°), respectively; with respect to the eye position, inward strabismus was found; and with respect to the primary eye position in the major amblyoscope, +18° R/L 1° Ex20° or more (un-measureable) in the left eye fixation was found. Maddox double rod test was performed, and outward rotation of about 30° was observed.

From clinical findings, bilateral superior oblique palsy caused by head trauma was diagnosed. For the purpose of alleviating homonymous and torsional diplopia, after twelve months from the first visit, the first surgical operation, that is, 6.5 mm of medial rectus muscle recession in the left eye and nasal transposition of one muscle width of inferior rectus muscle of the two eyes was performed under local anesthesia.

After two weeks from the first surgical operation, the eye position exhibited +16° L/R 3° Ex19° at the primary position in the left eye fixation with the major amblyoscope. Like this, the cyclodeviation was alleviated, and the homonymous torsional diplopia still remained. In addition, after the first surgical operation, the patient told that it was difficult to tell the state of the torsional diplopia during the surgical operation and he proposed that a certain objective visual mark would be presented.

Second Surgical Operation

The second surgical operation was performed after twelve months from the first surgical operation. The device according to the present invention was used before the surgical operation, during the surgical operation, and after the surgical operation. Before the surgical operation, the eye position (one month before the second surgical operation) exhibited +13° L/R 2° Ex18° at the primary position in the left fixation with the major amblyoscope, and the cyclodeviation measured by the device according to the present invention was Ex19° in the sitting posture and Ex19° in the supine position.

The second surgical operation was performed under local anesthesia. The cyclodeviation measurement during the surgical operation was performed in the supine position by using the device according to the present invention. In the surgical operation, first, with respect to the esotropia, the operation of 6.5 mm of medial rectus muscle recession in the right eye was performed in advance. After the surgical procedure, the cyclodeviation was Ex19°. Next, with respect to the cyclotropia, the operation of temporal transposition of one muscle width of superior rectus muscle of the right eye was performed. After the surgical procedure, the cyclodeviation was alleviated as Ex10°. However, since the torsional diplopia remained, the operation of temporal transposition of one muscle width of superior muscle of the left eye was additionally performed. As a result, the cyclodeviation became Ex6°, and the diplopia disappeared. Therefore, the surgical operation was finished. Ten days after the second surgical operation, the eye position was +6° Ex7° at the primary eye position in the left eye fixation with the major amblyoscope, and the cyclodeviation measured by the device according to the present invention was Ex7° in both of the sitting posture and the supine position. The post-operation course was so good that there was no complaint of the diplopia.

It can be understood from the result of the second surgical operation that, in a case where multiple surgical procedures are particularly scheduled as the treatment for the cyclotropia, if the correction effect can be checked by the deviation amount every surgical procedure, even in a case where the correction effect of the surgical procedures is insufficient, it is possible to perform extemporaneous responding such as changing or adding the surgical procedure while checking the residual strabismus angle. It is considered that this is useful to reduce the risk of over-correction or under-correction by the surgical operation and further to maintain a good eye position without diplopia after the surgical operation.

As described above, it can be understood that the device according to the present invention can perform the measurement irrespective of patient's posture and has a high quantitatively equivalent to that of the major amblyoscope, and is effective as a method of measuring the cyclodeviation. In addition, the cyclodeviation measurement during the surgical operation can be performed by using the device according to the present invention, so that it is possible to minimize the residual strabismus and the number of surgical operations. In addition, the device according to the present invention can accurately measure the cyclodeviation in a short time, the device is not limited to the use during the surgical operation, and the device is useful for screening the cyclotropia and observing the post-operation course in routine care.

Example 3: Evaluation of MB Type Cyclodeviation Measurement Device According to Present Invention in Diagnosis In this example, the MB type cyclodeviation measurement device illustrated in FIG. 5 was used as the device according to the present invention. The board is made of a black acrylic plate of 8 cm×13 cm×6 mm. Each of the diameter of the Bagolini striated lens and the diameter of the Maddox rod is 6 cm.

The subjects were 10 patients (19 to 82 years old) having strabismus who were observed to have cyclodeviation at the primary eye position. The cyclodeviation measurement was performed in nine-directional eye positions by using the device according to the present invention and the major amblyoscope. Differences among the measured values of the respective measurement points were checked. The measurement results were analyzed with the fixed eye as a starting point at divided views of frontal view, inward view, outward view, upward view, downward view, inner upward view, outer upward view, inner downward view, and outer downward view.

The average values±standard deviations of differences (values in the device according to the present invention− values by the major amblyoscope) of the measurement values in the device according to the present invention and the major amblyoscope were +0.3°±1.1° at the frontal view, +0.6°±2.4° at the inward view, +0.7°±2.5° at the outward view, +0.1°±1.7° at the upward view, −0.2°±1.7° at the downward view, +0.9°±1.6° at the inner upward view, −0.9°±2.1° at the outer upward view, +0.1°±1.6° at the inner downward view, and 0.0°±2.4° outer downward view. In any directional eye positions, similar results of the binocular examination were exhibited.

The measured values of the cyclodeviation by the device according to the present invention are similar to those of the major amblyoscope, and thus, it is considered that the device according to the present invention have a quantitatively equivalent to that of the major amblyoscope. It is confirmed that the device according to the present invention is small-sized and simple, can perform quantitative cyclodeviation measurement in nine-directional eye positions, and is useful for routine care about strabismus.

A cyclodeviation measurement device according to the present invention can be used for diagnosis of strabismus, and the cyclodeviation measurement device can be used to check of correction effects of surgical procedure during surgical operation.

While the present invention has been described above with reference to specific embodiments, modifications and improvements obvious to the ordinarily skilled in the art are included within the scope of the present invention.

The invention claimed is:

1. A cyclodeviation measurement device, comprising:
a pair of a Maddox rod and a Bagolini striated lens;
a lens holding means capable of holding the Maddox rod and the Bagolini striated lens so that the Maddox rod is rotatable;
a manipulation means capable of freely rotating the Maddox rod; and
an indication means indicating a rotation angle of the Maddox rod.

2. The cyclodeviation measurement device according to claim 1, wherein the Bagolini striated lens is interchangeable with a Maddox rod.

3. A cyclodeviation measurement device, comprising:
a board;
a pair of Maddox rods provided on the board so that at least one of the Maddox rods is rotatable;
a manipulation means capable of freely rotating the rotatable Maddox rod; and
an indication means indicating a rotation angle of the Maddox rod.

4. The cyclodeviation measurement device according to claim 3, wherein one of the Maddox rods is interchangeable with the Bagolini striated lens.

\* \* \* \* \*